(12) United States Patent
Quay et al.

(10) Patent No.: US 7,812,120 B2
(45) Date of Patent: Oct. 12, 2010

(54) NASAL CALCITONIN FORMULATIONS CONTAINING CHLOROBUTANOL

(75) Inventors: Steven C. Quay, Edmonds, WA (US);
Jorge C. de Meireles, Syosset, NY (US); Arati A. Deshpande, Miller Place, NY (US); Zenaida O. Go, Clifton, NJ (US); Anthony P. Sileno, Brookhaven Hamlet, NY (US)

(73) Assignee: Par Pharmaceutical, Inc., Woodcliff Lake, NJ (US)

( * ) Notice: Subject to any disclaimer, the term of this patent is extended or adjusted under 35 U.S.C. 154(b) by 406 days.

(21) Appl. No.: 10/805,788

(22) Filed: Mar. 22, 2004

(65) Prior Publication Data
US 2004/0224890 A1  Nov. 11, 2004

Related U.S. Application Data

(60) Provisional application No. 60/456,921, filed on Mar. 21, 2003.

(51) Int. Cl.
*A61K 38/00* (2006.01)
(52) U.S. Cl. .................................... 530/307
(58) Field of Classification Search .................... None
See application file for complete search history.

(56) References Cited

U.S. PATENT DOCUMENTS

| | | | |
|---|---|---|---|
| 4,670,419 A | 6/1987 | Uda et al. | |
| 4,690,952 A | 9/1987 | Kagatani et al. | |
| 4,788,221 A | 11/1988 | Kagatani et al. | |
| 4,985,242 A | 1/1991 | Sekine et al. | |
| 4,988,512 A | 1/1991 | Azria | |
| 5,026,825 A | 6/1991 | Grebow et al. | |
| 5,059,587 A | 10/1991 | Yamamoto et al. | |
| 5,091,365 A | 2/1992 | Sandow et al. | |
| 5,112,804 A | 5/1992 | Kowarski | |
| 5,124,315 A | 6/1992 | Ceschel et al. | |
| 5,153,308 A | 10/1992 | Sugiyama et al. | |
| 5,179,079 A | 1/1993 | Hansen et al. | |
| 5,183,802 A | 2/1993 | Aliverti et al. | |
| 5,200,393 A | 4/1993 | Weiner | |
| 5,204,108 A | 4/1993 | Illum | |
| 5,211,950 A | 5/1993 | Kobayashi et al. | |
| 5,215,739 A | 6/1993 | Kamishita et al. | |
| 5,281,580 A | 1/1994 | Yamamoto et al. | |
| 5,321,008 A | 6/1994 | Beaumont et al. | |
| 5,428,006 A | 6/1995 | Bechgaard et al. | |
| 5,482,706 A | 1/1996 | Igari et al. | |
| 5,482,931 A | 1/1996 | Harris et al. | |
| 5,503,827 A | 4/1996 | Woog et al. | |
| 5,508,260 A | 4/1996 | Beaumont et al. | |
| 5,514,365 A | 5/1996 | Mardente et al. | |
| 5,527,771 A | 6/1996 | Beaumont et al. | |
| 5,554,378 A | 9/1996 | Uda et al. | |
| 5,565,423 A | 10/1996 | Sandow et al. | |
| 5,574,006 A | 11/1996 | Yanagawa | |
| 5,576,016 A | 11/1996 | Amselem et al. | |
| 5,578,324 A | 11/1996 | Dohi et al. | |
| 5,603,943 A | 2/1997 | Yanagawa | |
| 5,654,000 A | 8/1997 | Poli et al. | |
| 5,681,811 A | 10/1997 | Ekwuribe | |
| 5,693,608 A | 12/1997 | Bechgaard et al. | |
| 5,719,122 A | 2/1998 | Chiodini et al. | |
| 5,725,852 A | 3/1998 | Igari et al. | |
| 5,725,871 A | 3/1998 | Illum | |
| 5,733,569 A | 3/1998 | Azria et al. | |
| 5,759,565 A * | 6/1998 | Azria et al. ................. 424/434 |
| 5,859,048 A | 1/1999 | Oohashi et al. | |
| 5,948,749 A | 9/1999 | Igarashi et al. | |
| 6,087,338 A | 7/2000 | Veronesi et al. | |
| 6,149,893 A | 11/2000 | Mardente et al. | |
| 6,161,731 A | 12/2000 | Sigg | |
| 6,174,857 B1 | 1/2001 | Burk | |
| 6,221,367 B1 | 4/2001 | Milstein et al. | |
| 6,665,421 B1 | 12/2003 | Farina | |
| 2002/0010428 A1 | 1/2002 | Vedrine et al. | |
| 2002/0012688 A1 | 1/2002 | Dohi et al. | |
| 2002/0015737 A1 | 2/2002 | Shih | |
| 2002/0031558 A1 | 3/2002 | Yoo | |
| 2002/0037836 A1 | 3/2002 | Henriksen | |
| 2002/0068092 A1 | 6/2002 | Bosch et al. | |
| 2002/0076441 A1 | 6/2002 | Shih | |
| 2002/0107265 A1 | 8/2002 | Chen et al. | |
| 2002/0110525 A1 | 8/2002 | Adjei et al. | |

(Continued)

FOREIGN PATENT DOCUMENTS

EP  0115627  * 12/1982

(Continued)

OTHER PUBLICATIONS http://www.webster.com/dictionary/composition Definition of Composition.*

(Continued)

*Primary Examiner*—Cecilia Tsang
*Assistant Examiner*—Thomas S Heard
(74) *Attorney, Agent, or Firm*—Foley & Lardner LLP

(57) ABSTRACT

Compositions suitable for intranasal administration containing calcitonin, chlorobutanol, a pH of about 3.5, and sodium chloride, and an intranasal spray and a pharmaceutical delivery device thereof.

19 Claims, 1 Drawing Sheet

U.S. PATENT DOCUMENTS

| | | |
|---|---|---|
| 2002/0110527 A1 | 8/2002 | Zhu et al. |
| 2002/0110528 A1 | 8/2002 | Zhu et al. |
| 2003/0018416 A1 | 1/2003 | Farina et al. |

FOREIGN PATENT DOCUMENTS

| | | |
|---|---|---|
| EP | 0 111 841 A1 | 6/1984 |
| EP | 0 115 627 A1 | 8/1984 |
| EP | 0 183 527 B1 | 6/1986 |
| EP | 0 193 372 A2 | 9/1986 |
| EP | 0 358 234 A2 | 3/1990 |
| EP | 0 371 010 A1 | 5/1990 |
| EP | 0 418 697 A1 | 3/1991 |
| EP | 0 471 618 A1 | 8/1991 |
| EP | 0 489 217 A1 | 6/1992 |
| GB | 2 177 914 A | 2/1987 |
| WO | WO 99/16427 | 4/1999 |

OTHER PUBLICATIONS

Physicians Desk Reference, 2002 edition, p. 2375.

Hallen et al., "Benzalkonium Chloride in Nasal Decongestive Sprays has a Long-Lasting Adverse Effect on the Nasal Mucosa of Healthy Volunteers," *Clin. Exp. Allergy*, vol. 25, pp. 401-405 (1995).

Berg et al., "The Effect of Decongestive Nosedrops on Human Respiratory Mucosa in Vitro," *Larynogoscope*, 104: pp. 1153-1158 (1994).

Braga et al., "The Effects of Calcitonin Nasal Preparations and Their Excipients on Mucociliary Clearance in an Ex-Vivo Frog Palate Test," *J. Pharm. Pharmacol.*, 44: pp. 938-940 (1992).

\* cited by examiner

NASAL CALCITONIN FORMULATIONS CONTAINING CHLOROBUTANOL

This claims the benefit under 35 U.S.C.§119 (e) of U.S. Provisional Application No. 60/456,921 filed on Mar. 21, 2003, the entire contents of which are incorporated herein by reference.

BACKGROUND OF THE INVENTION

The teachings of all of the references cited herein are incorporated herein by reference.

Calcitonin is a polypeptide hormone secreted by the parafollicular cells of the thyroid gland in mammals and by the ultimobrancial gland of birds and fish. Synthetic salmon calcitonin is produced and sold by Novartis Pharmaceuticals Corporation (East Hanover, N.J.). It is used to treat a variety of conditions including postmenopausal osteoporosis, symptomatic Paget's disease of bone, and hypercalcemia. Calcitonins have been extracted from a number of sources including salmon, porcine, eel and human. Calcitonins with amino acid sequences identical to the natural forms have been produced by chemical synthesis as well as by recombinant technology.

Currently calcitonin is administered either by subcutaneous or intramuscular injections or it is administered intranasally. Intranasal administration of calcitonin is disclosed in U.S. Pat. No. 5,759,565. The nasal formulation was designed to be stored in a multi-dose container that was stable for an extended period of time and resisted microbial contamination. The preservative in the formulation, benzalkonium chloride has been shown to aggravate rhinitis in healthy volunteers who were given a decongestant nasal spray containing the preservative, and allergic reactions to the intranasal salmon calcitonin spray MIACALCIN® have been reported, including one of anaphylactic shock. This is believed to be due to the preservative benzalkonium chloride because the patient could tolerate injectable salmon calcitonin, which contains no benzalkonium chloride, without incident. See the 'Physicians Desk Reference' 2002 edition page 2375 (Medical Economics, Montvale, N.Y.). Benzalkonium chloride also has adverse (Hallen, H et. al., *Clin. Exp. Allergy* 25: 401-405 (1995). Also studies have shown that when respiratory mucosal tissue is exposed to benzalkonium chloride in vitro, the tissue underwent severe morphological alterations, Berg et al., *Larynogoscope*, 104:153-1158 (1994). Benzalkonium chloride also caused significant slowing of the mucociliary transport velocity in the ex vivo frog palate test, Braga, P. C., et al., *J. Pharm. Pharmacol.* 44:938-940 (1992).

Thus, there is a need for a new formulation of intranasal calcitonin that contains a preservative other than benzalkonium chloride.

DESCRIPTION OF THE INVENTION

Figure 2:
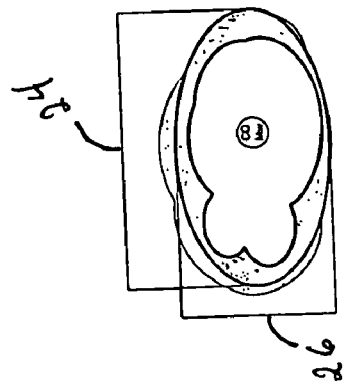
FIG. 2 shows the spray pattern produced by the actuator wherein 24 represents the major axis and 26 represent the minor axis.

The present invention fills this need by providing for an intranasal formulation of calcitonin comprised of calcitonin, preferably salmon calcitonin, chlorobutanol at a concentration of less than 0.4% weight/weight, and water and having a pH of less than 4 with the proviso that benzalkonium chloride is not present in the formulation. The preferred pH of the solution is about between 3 to 4, most preferably 3.5. The preferred formulation is comprised of 0.25% weight/weight of chlorobutanol, 0.85% sodium chloride, 0.0355% calcitonin and 98.86% purified water and the pH is about 3.5.

The prior art teaches away from the use of chlorobutanol stating that at 0.6% concentration, the chlorobutanol caused more than 50% inhibition of ciliary beating frequency of rat trachea. However according to the present invention, this effect is greatly reduced when the concentration of chlorobutanol is less than 0.4% and totally eliminated at a concentration of around 0.25%. The prior art also teaches that chlorobutanol at 0.6% in calcitonin nasal pharmaceutical compositions showed insufficient activity against the test fungus *Penicillium steckii*. However, according to the present invention, it has been discovered that chlorobutanol is very effective in inhibiting the growth of *Penicillium steckii*, when the concentration of chlorobutanol is less than 0.4% and the pH of the calcitonin solution is less than 4.

In accordance with the present invention, it has now been surprisingly been discovered that an intranasal formulation of calcitonin can be produced that are stable, inhibit the growth of *Penicillium steckii* and do not inhibit the ciliary beating frequency of rat trachea wherein the preservative used is chlorobutanol at a concentration of less than 0.4% wherein the pH is less than 4.

Accordingly, the present invention provides, in a first aspect, a pharmaceutical solution for nasal administration comprising:

i) a calcitonin, ii) chlorobutanol at a concentration less than 0.4% and iii) a liquid diluent or carrier suitable for application to the nasal mucosa wherein the pH of the solution is less than 4, with the proviso that the solution does not contain benzalkonium chloride due to the allergic nature of benzalkonium chloride.

The term "calcitonin" is used throughout the present specification and claims to include not only the natural calcitonins, but also their pharmaceutically active derivatives and analogues, e.g. in which one or more of the amino acid residues present in the naturally occurring product is replaced, or in which the amino or carboxyl terminus of the polypeptide is modified. Preferred calcitonins for use in accordance with the present invention include salmon, human, porcine and eel calcitonins. All of these calcitonins are commercially available The calcitonins for use in the present invention may be in free form or in pharmaceutically acceptable salt or complex form, e.g., in pharmaceutically acceptable acid addition salt form. Such salts and complexes are known and possess an equivalent degree of activity and tolerability to the free forms. Suitable acid addition salt forms for use in accordance with the invention include for example the hydrochlorides and acetates.

The above-described calcitonin solutions are designed to be administered to the nasal mucosa either in drop or in spray form. However, the preferred mode of administration is in spray form, i.e., in the form of finely divided droplets. An example of a suitable spray pump is the Pfeiffer Spray Pump Model # 63385 produced by Pfeiffer GmbH, Radolfzell, Germany.

Aerosol Nasal Administration of Calcitonin

Calcitonin is administered intranasally using a nasal spray or aerosol according to the present invention. In this area the following definitions are useful.
1. Aerosol—A product that is packaged under pressure and contains therapeutically active ingredients that are released upon activation of an appropriate valve system.
2. Metered aerosol—A pressurized dosage form comprised of metered dose valves, which allow for the delivery of a uniform quantity of spray upon each activation.
3. Powder aerosol—A product that is packaged under pressure and contains therapeutically active ingredients in the form of a powder, which are released upon activation of an appropriate valve system.
4. Spray aerosol—An aerosol product that utilizes a compressed gas as the propellant to provide the force necessary to expel the product as a wet spray; it generally applicable to solutions of medicinal agents in aqueous solvents.
5. Spray—A liquid minutely divided as by a jet of air or steam. Nasal spray drug products contain therapeutically active ingredients dissolved or suspended in solutions or mixtures of excipients in nonpressurized dispensers.
6. Metered spray—A non-pressurized dosage form consisting of valves that allow the dispensing of a specified quantity of spray upon each activation.
7. Suspension spray—A liquid preparation containing solid particles dispersed in a liquid vehicle and in the form of course droplets or as finely divided solids.

The fluid dynamic characterization of the aerosol spray emitted by metered nasal spray pumps as a drug delivery device ("DDD"). Spray characterization is an integral part of the regulatory submissions necessary for Food and Drug Administration ("FDA") approval of research and development, quality assurance and stability testing procedures for new and existing nasal spray pumps.

Thorough characterization of the spray's geometry has been found to be the best indicator of the overall performance of nasal spray pumps. In particular, measurements of the spray's divergence angle (plume geometry) as it exits the device; the spray's cross-sectional ellipticity, uniformity and particle/droplet distribution (spray pattern); and the time evolution of the developing spray have been found to be the most representative performance quantities in the characterization of a nasal spray pump. During quality assurance and stability testing, plume geometry and spray pattern measurements are key identifiers for verifying consistency and conformity with the approved data criteria for the nasal spray pumps.

Definitions

Plume Height—the measurement from the actuator tip to the point at which the plume angle becomes non-linear because of the breakdown of linear flow. Based on a visual examination of digital images, and to establish a measurement point for width that is consistent with the farthest measurement point of spray pattern, a height of 30 mm is defined for this study Major Axis—the largest chord that can be drawn within the fitted spray pattern that crosses the COMw in base units (mm)

Minor Axis—the smallest chord that can be drawn within the fitted spray pattern that crosses the COMw in base units (mm)

Ellipticity Ratio—the ratio of the major axis to the minor axis $D_{10}$—the diameter of droplet for which 10% of the total liquid volume of sample consists of droplets of a smaller diameter (μm)

$D_{50}$—the diameter of droplet for which 50% of the total liquid volume of sample consists of droplets of a smaller diameter (μm), also known as the mass median diameter $D_{90}$—the diameter of droplet for which 90% of the total liquid volume of sample consists of droplets of a smaller diameter (μm)

Span—measurement of the width of the distribution, The smaller the value, the narrower the distribution. Span is calculated as $(D_{90}-D_{10})/D_{50}$.

% RSD—percent relative standard deviation, the standard deviation divided by the mean of the series and multiplied by 100, also known as % CV.

Figure 1B:
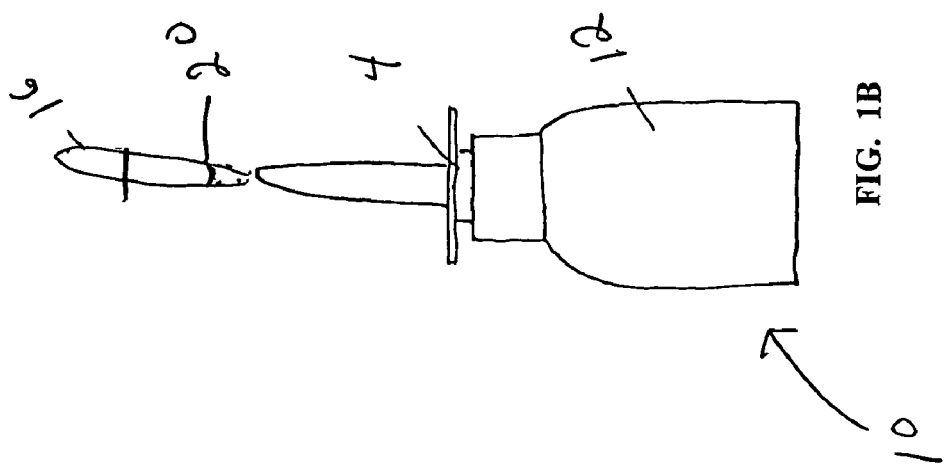
FIG. 1B shows the nasal spray pump/actuator that is engaged and expelling a spray plume.
Figure 1A:
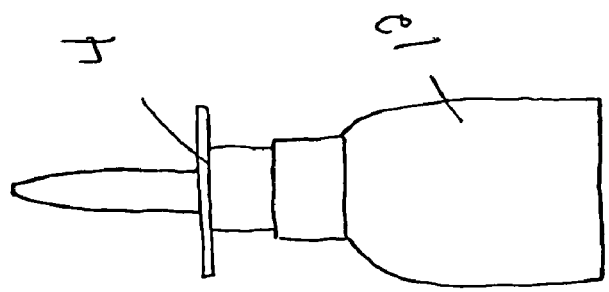
FIG. 1A shows a nasal spray pump/actuator that is not engaged.

FIGS. 1A and 1B show a nasal spray device 10 before engagement (FIG. 1A) and after engagement (FIG. 1B). The nasal spray bottle 10 is comprised of a bottle 12 into which the calcitonin formulation is placed, and an actuator 14, which when actuated or engage forces a spray plume, 16, of the calcitonin out of the spray bottle, 12, through the actuator, 14. A spray pattern is determined by taking a photograph of a cross-section of the spray plume 16 above a predetermined height, 18, of the plume. The spray plume also has angle of ejection, 20, as it leaves actuator, 14. A spray pattern of spray plume 16 is shown on FIG. 2. Spray pattern 2, is elliptical and has a major axis, 24, and a minor axis 26.

The compositions of the present invention may of course also include additional ingredients, in particular components belonging to the class of conventional pharmaceutically applicable surfactants.

Preferably, the liquid pharmaceutical calcitonin composition of the present invention contains a pharmaceutically acceptable, a liquid diluent or carrier for application to the nasal mucosa, most preferably aqueous saline.

The calcitonin solutions of the present invention are formulated so as to permit administration via the nasal route. For this purpose they may also contain additional ingredients including, for example, ciliary stimulants such as caffeine.

Generally, for nasal administration a mildly acid pH is preferred. Preferably the calcitonin solutions of the present invention will have a pH of from 3 to 4, more preferably about 3.5. Adjustment of the pH is achieved by addition of an appropriate acid, such as hydrochloric acid.

The calcitonin solutions of the present invention should also possess an appropriate isotonicity and viscosity. Preferably, they have an osmotic pressure of from about 260 to about 380 mOsm/liter. Desired viscosity for the nasal spray is preferably less than 0.98 cP.

The amount of calcitonin to be administered according to the method of the present invention will depend upon the particular calcitonin chosen, the condition treated, the desired frequency of administration and the effect desired. Generally the concentration of calcitonin in solution should be about 2200 International Units (I.U.) per ml. If 0.09 mL is administered per actuation, this administers 200 I.U. to the patient. The International Units are based upon a bioassay in comparison with the International Reference Preparation of calcitonin-salmon for Bioassay, distributed by the National Institute of Biologic Standards and Control.

For the purposes of nasal administration, the calcitonin solutions of the present invention will be placed in a nasal applicator device. Suitable applicators are known in the art and include those adapted for administration of liquid compositions to the nasal mucosa in drop or spray form. Since dosing with calcitonins should be as accurately controlled as possible use of spray applicators for which the administered quantity is susceptible to precise regulation will generally be preferred. Suitable administrators include atomizing devices such as pump-atomizers and aerosol dispensers. The atomizing device will be provided with an appropriate spray adaptor allowing delivery of the calcitonin solution to the nasal mucosa.

EXAMPLE 1

Preparation of Salmon Calcitonin Solution

A 1200 gram batch of the preferred calcitonin solution of the present invention was prepared according to the following procedure and was comprised of the following ingredients.

TABLE 1

| Ingredient Name | % Weight/Weight | Weight per 1200 gram Batch |
|---|---|---|
| Chlorobutanol anhydrous, NF | 0.25% | 3.00 |
| Sodium Chloride, USP | 0.85 | 10.2 |
| Salmon Calcitonin, EP-Potency of 6236 IU/mg | 0.0355 | 0.426 |
| 1 % Hydrochloric Acid, NF | Added as needed to adjust pH to 3.5 | |
| Purified Water, USP Nitrogen, NF | 98.86 | 1186.32 |

Procedure

Into a 3 Q stainless steel beaker was placed 1186.32 grams of water and the beaker was covered with parafilm and the water was purged with nitrogen, NF and stirred. With continuous stirring and purging with nitrogen, 3.00 grams of chlorobutanol, (Spectrum Chemicals & Laboratory Supplies, Inc., Gardena, Calif.) was added to the water. Into the solution was then added 10.2 g of sodium chloride (Mallinckrodt, Inc. St. Louis, Mo.). After the sodium chloride was dissolved, the oxygen content was determined, and the solution was further purged with nitrogen until the oxygen content was less than 5%. Into the solution was added 0.426 g of calcitonin, EP (BACHEM California, Inc, Gardena, Calif.). Into the solution was added 1% HCl until the pH of the solution was adjusted to 3.5. The weight of the solution was determined and a sufficient amount of water was added to bring the weight of the solution to 1200 g. The oxygen content was again determined, and the solution was further purged with nitrogen until the oxygen content of the solution was less than 5% by volume.

EXAMPLE 2

This example describes a pharmaceutical composition product comprising an aqueous solution formulation of salmon calcitonin at a concentration sufficient to produce therapeutically effective plasma concentrations and an actuator to produce an aerosol of said solution, wherein the spray pattern ellipticity ratio of said aerosol is between 1.00 and 1.40 when measured at a height of 30 cm distance from the actuator tip.

The volume of the aerosol can be between about 5 microliters and 1.0 ml, preferably between 20 and 200 microliters.

This test method describes the procedure for characterizing plume geometry of the calcitonin nasal solution formulations using the SprayView NSP system. The plume geometry is characterized using a SprayView High Speed Optical Spray Characterization System (SprayView NSP) with Integrated SprayView NSx actuation station (Image Therm Engineering, Inc., Sudbury, Mass.) according to the methods described in U.S. Pat. No. 6,665,421 and U.S. Patent Application Publication No. 20030018416 published Jan. 23, 2003.

Using the formulation of table 1 the spray characterization and droplet size of the formulation in both a 1 mL and a 3 mL bottle both having a nasal Spray Pump w/Safety Clip, Pfeiffer SAP # 63385, which delivers a dose of 0.1 mL per squirt and has a diptube length of 36.05 mm.

The droplet size data are shown in the following table.

| Droplet Size for Nasal Spray Bottle and Pfeiffer SAP # 60548 | | | | | | |
|---|---|---|---|---|---|---|
| | | $D_{10}$ | $D_{50}$ | $D_{90}$ | Span | % < 10 micrometer |
| 1 mL | Salmon calcitonin | 14.0 | 32.7 | 94.4 | 2.4 | 4.1 |

Below are listed the spray pattern results

| Spray Pattern | | MajorAxis | MinorAxis | EllipticityRatio |
|---|---|---|---|---|
| active | 1 mL | 31.2 mm | 27.4 mm | 1.15 |

What is claimed is:

1. A method for intranasal administration of calcitonin which comprises administering intranasally to an individual a solution of calcitonin consisting of calcitonin, chlorobutanol at a concentration of 0.25% weight/weight, and water and having a pH of about 3.5, sodium chloride at a concentration of about 0.85%, and optionally hydrochloric acid in an amount sufficient to adjust the pH of the solution to about 3.5, and wherein the aqueous solution has an oxygen at a content of less than about 5%.

2. The method of claim 1 wherein the calcitonin is present in solution at a concentration of about 0.0355 weight/weight.

3. The method of claim 1 wherein the calcitonin formulation is administered into a nose of an individual through an actuator tip as a spray, wherein the spray has a spray pattern ellipticity ratio of from about 1.0 to about 1.4 when measured at a height of 3.0 cm from the actuator tip.

4. The method of claim 3 wherein the spray produces droplets, wherein less that 5% of the droplets are less than 10 microns in size.

5. The method of claim 3 wherein the spray has a spray pattern major axis of about 31.2 mm and a minor axis of about 27.4 mm.

6. A composition consisting of:
an aqueous solution of calcitonin at a concentration of about 0.0355% weight/weight;
chlorobutanol at a concentration of between about 0.25% and about 0.4% weight/weight;
sodium chloride at a concentration of about 0.85% weight/weight;
wherein the solution has a pH between about 3 to 4 and less than about 5% oxygen;

wherein the composition is suitable for intranasal administration in humans.

7. A composition consisting of:
an aqueous solution of salmon calcitonin at a concentration of 2200 International Units (I.U.) per ml;
chlorobutanol at a concentration of between 0.25% and about 0.4% weight/weight;
sodium chloride at a concentration of 0.85% weight/weight;
wherein the solution has a pH between about 3 to 4 and less than about 5% oxygen; and
wherein the composition is suitable for intranasal administration in humans.

8. A pharmaceutical composition consisting of:
an aqueous solution of salmon calcitonin at a concentration of 2200 International Units (I.U.) per ml;
chlorobutanol at a concentration of between 0.25% and about 0.4% weight/weight;
sodium chloride at a concentration of 0.85% weight/weight;
wherein the solution has a pH between about 3 to 4 and less than about 5% oxygen; and
wherein the composition is suitable for intranasal administration in humans.

9. A pharmaceutical device comprising a composition according to claim 6 and an actuator to produce an aerosol spray of the composition, the spray having a spray pattern ellipticity ratio of from about 1.0 to about 1.4 when measured at a height of 3.0 cm from the actuator tip.

10. A pharmaceutical device comprising a composition according to claim 6 and an actuator to produce an aerosol spray of the composition, wherein the spray has a spray pattern major axis of about 31.2 mm and a minor axis of about 27.4 mm.

11. A pharmaceutical device comprising a composition according to claim 6 and an actuator to produce an aerosol spray of the composition, the spray having a spray pattern ellipticity ratio of from about 1.0 to about 1.4 when measured at a height of 3.0 cm from the actuator tip, wherein less than 5% of the droplets are smaller than 10 microns in size.

12. A pharmaceutical device comprising a composition according to claim 7 and an actuator to produce an aerosol spray of the composition, the spray having a spray pattern ellipticity ratio of from about 1.0 to about 1.4 when measured at a height of 3.0 cm from the actuator tip.

13. A pharmaceutical device comprising a composition according to claim 7 and an actuator to produce an aerosol spray of the composition, wherein the spray has a spray pattern major axis of about 31.2 mm and a minor axis of about 27.4 mm.

14. A pharmaceutical device comprising a composition according to claim 7 and an actuator to produce an aerosol spray of the composition, the spray having a spray pattern ellipticity ratio of from about 1.0 to about 1.4 when measured at a height of 3.0 cm from the actuator tip, wherein less than 5% of the droplets are smaller than 10 microns in size.

15. A pharmaceutical device comprising a composition according to claim 8 and an actuator to produce an aerosol spray of the composition, the spray having a spray pattern ellipticity ratio of from about 1.0 to about 1.4 when measured at a height of 3.0 cm from the actuator tip.

16. A pharmaceutical device comprising a composition according to claim 8 and an actuator to produce an aerosol spray of the composition, wherein the spray has a spray pattern major axis of about 31.2 mm and a minor axis of about 27.4 mm.

17. A pharmaceutical device comprising a composition according to claim 8 and an actuator to produce an aerosol spray of the composition, the spray having a spray pattern ellipticity ratio of from about 1.0 to about 1.4 when measured at a height of 3.0 cm from the actuator tip, wherein less than 5% of the droplets are smaller than 10 microns in size.

18. A composition consisting of a solution of (i) calcitonin at a concentration of about 0.0355% weight/weight; (ii) chlorobutanol at a concentration of equal to or greater than about 0.25% and less than about 0.4% weight/weight; (iii) water; (iv) sodium chloride at a concentration of about 0.85% weight/weight:; and optionally (v) hydrochloric acid; wherein the composition has a pH of 4 or less; and wherein the composition is suitable for intranasal administration in humans.

19. A composition consisting of a solution of calcitonin at a concentration of 2200 International Units (I.U.) per ml, chlorobutanol at a concentration of about 0.25% weight/weight, water, sodium chloride at a concentration of 0.85% weight/weight, and optionally hydrochloric acid, wherein the composition has a pH of 4 or less, and wherein the composition is suitable for intranasal administration in humans.

* * * * *